US007943597B2

(12) United States Patent
Lewis et al.

(10) Patent No.: US 7,943,597 B2
(45) Date of Patent: May 17, 2011

(54) PHOSPHATE-BINDING CHITOSAN AND USES THEREOF

(75) Inventors: Robert L. Lewis, Madison, MS (US); Charles E. Day, Leitchfield, KY (US)

(73) Assignee: Cypress Pharmaceutical, Inc., Madison, MS (US)

( * ) Notice: Subject to any disclaimer, the term of this patent is extended or adjusted under 35 U.S.C. 154(b) by 0 days.

(21) Appl. No.: 12/099,433

(22) Filed: Apr. 8, 2008

(65) Prior Publication Data
US 2008/0193521 A1    Aug. 14, 2008

(51) Int. Cl.
A61K 31/722 (2006.01)
A61K 31/715 (2006.01)
(52) U.S. Cl. .............................. 514/55; 514/54; 536/20
(58) Field of Classification Search .................... 514/55, 514/54; 536/20
See application file for complete search history.

(56) References Cited

U.S. PATENT DOCUMENTS

| | | | |
|---|---|---|---|
| 5,116,747 | A | 5/1992 | Moo-Young et al. |
| 5,770,187 | A | 6/1998 | Hasebe et al. |
| 6,638,918 | B2 | 10/2003 | Davison et al. |
| 6,740,752 | B2 | 5/2004 | Struszcyk et al. |
| 7,192,395 | B1 | 3/2007 | Qu et al. |
| 7,195,675 | B2 * | 3/2007 | Okazaki et al. ................. 127/29 |
| 7,288,532 | B1 | 10/2007 | Payne et al. |
| 2001/0051150 | A1 | 12/2001 | Ranganathan et al. |
| 2005/0085443 | A1 | 4/2005 | Chinachoti et al. |
| 2008/0125394 | A1 | 5/2008 | Savica |

FOREIGN PATENT DOCUMENTS

| | | |
|---|---|---|
| AU | 9662988 | 1/1997 |
| CN | 1312295 | 9/2001 |
| CN | 1364815 | 8/2002 |
| CN | 1401616 | 3/2003 |
| CN | 1403158 | 3/2003 |
| CN | 1593385 | 3/2005 |
| CN | 1593434 | 3/2005 |
| CN | 1618959 | 5/2005 |
| CN | 1629197 | 6/2005 |
| CN | 1683441 | 10/2005 |
| CN | 1687448 | 10/2005 |
| CN | 1736928 | 2/2006 |
| CN | 1746193 | 3/2006 |
| CN | 1769440 | 5/2006 |
| CN | 1799647 | 7/2006 |
| CN | 1846788 | 10/2006 |
| CN | 1869105 | 11/2006 |
| CN | 1927075 | 3/2007 |
| CN | 1935339 | 3/2007 |
| CN | 101011606 | 8/2007 |
| DE | 195 28 524 A1 | 2/1997 |
| JP | 60160900 | 8/1985 |
| JP | 08239311 | 9/1996 |
| JP | 11021302 | 1/1999 |
| JP | 11253541 | 9/1999 |
| JP | 2000270809 | 10/2000 |
| JP | 2002338602 | 11/2002 |
| KR | 2001099264 | 11/2001 |
| KR | 2002063422 | 8/2002 |
| KR | 2005108819 | 11/2005 |
| KR | 2007014260 | 2/2007 |
| RU | 2215749 | 11/2003 |
| RU | 2255924 | 7/2005 |
| WO | WO 9701629 | 1/1997 |
| WO | WO-0047177 A1 | 8/2000 |
| WO | WO-0132751 A1 | 5/2001 |
| WO | WO 2005027885 | 5/2005 |
| WO | WO 2006/050314 A | 5/2006 |
| WO | WO 2006/061336 A | 6/2006 |
| WO | WO 2006/061336 A2 * | 6/2006 |
| WO | WO 2007/115973 A | 10/2007 |
| WO | WO 2007/115973 A2 * | 10/2007 |

OTHER PUBLICATIONS ntp.niehs.nih.gov; "Limited Summary of Data for Chemical Selection" (1999), pp. 1-16.*
International Search Report for PCT/US03/059634 (Jan. 22, 2009).
Written Opinion for PCT/US03/059634 (Jan. 22, 2009).
Behets, G.J., et al., "Effects of efficient phosphate binding on bone in chronic renal failure", Renal Failure, 27(4), pp. 475-484 (2005).
Savica, V., et al., "Nutritional therapy in chronic kidney disease", Nutrition in Clinical Care, 8(2), pp. 70-76 (2005).
Abdel-Naby, et al., "Preparation and some properties of immobilized Penicillium funiculosum 258 dextranase", Process Biochemistry (Oxford), 34(4), pp. 391-398 (1999).
Amuda, et al., "Removal of heavy metal from Industrial wastewater using modified activated coconut shell carbon", Biochemical Engineering Journal, 36(2), pp. 174-181 (2007).
Bernard, et al., Tight attachment of chitin-binding-domain-tagged proteins to surfaces coated with acetylated chitosan, Analytical biochemistry, 372(2), pp. 278-283 (2004).
Bhattarai, et al., "Acylated chitosan stabilized iron oxide nanoparticles as a novel nano-matrix and ceramic modification", Carbohydate Polymers, 69(3), pp. 467-477 (2007).
Chen, et al., "Breeding of chitosanase producing strain and study on its fermentation condition", Shipin Yu Fajiao Gongye, 30(3), pp. 66-69 (2004) (English Abstract Only).
Chen, et al., "Preparation and physical properties of chitosan-polyvinyl alcohol thermosensitive hydrogel", Qinghua Daxue Xuebao, Ziran Kexueban, 46(6), pp. 843-846 (2006) (English Abstract Only).
Chen, et al., "Preparation of superparamagnetic hydroxyapatite/chitosan rods", Cailiao Yanjiu Xuebao, 20(3), pp. 250-254 (2006) (English Abstract Only).
Dambies, et al., "As(v) removal from dilute solutions using MCIB (molybdate-impregnated chitosan beads)", Process Metallurgy, 9B(Biohydrometallurgy and the Environment Toward the Mining of the 21$^{st}$ Century, Pt. B), pp. 277-287 (1999) (English Abstract Only).
Dambies, et al., "As(V) sorption on molybdate-impregnated chitosan gel beads (MICB)", Advances in Chitin Science, 4(EUCHIS'99), pp. 302-309 (2000) (English Abstract Only).
Dambies, et al., "Treatment of arsenic-containing solutions using chitosan derivatives: uptake mechanism and sorption performances", Water Research, 36(15), pp. 3699-3710 (2002).

(Continued)

Primary Examiner — Shaojia Anna Jiang
Assistant Examiner — Michael C Henry
(74) Attorney, Agent, or Firm — Choate, Hall & Stewart LLP; Fangli Chen

(57) ABSTRACT

The present invention provides compositions and methods for removing phosphate from a subject using chitosan. The present invention also provides compositions and methods for treating hyperphosphatemia based on phosphate-binding chitosan.

22 Claims, No Drawings

OTHER PUBLICATIONS

Duan, et al., "Optimization of Trichoderma viride fermentation for manufacturing chitosanase", Zhejiang Gongye Daxue Xuebao, 35(1), pp. 41-45 (2007) (English Abstract Only).

Ekowati, et al., Biochemical characteristics of chitosanase from the Indonesian *Bacillus licheniformis* MB-2, Molecular Biotechnology, 33(2) (2006).

Fu, et al., "Analysis of natural carbohydrate biopolymer-high molecular chitosan and carboxymethyl chitosan by capillary zone electrophoresis", Carbohydrate Polymers, 68(3), pp. 511-516 (2007).

Gao, et al., "Drug membrane preparation and release character of gelatin-chitosan", Wuhan Ligong Daxue Xuebao, 27(11), pp. 24-26 (2005) (English Abstract Only).

Ghanem, et al., "Effect of preparation method on the capture and release of biologically active molecules in chitosan gel beads", Journal of Applied Polymer Science, 84(2), pp. 405-413 (2002).

Gupta, et al., Preparation and characterization of sodium hexameta phosphate cross-linked chitosan microspheres for controlled and sustained delivery of centchroman, International Journal of Biological Macromolecules, 38(3-5), pp. 272-283 (2006).

Hamdine, et al., "Effect of organic and inorganic acids on concentrated chitosan solutions and gels", International Journal of Biological Macromolecules, 37(3), pp. 134-142 (2005).

Hassan, et al., "Production of a pullulanase by *Penicillium oxalicum* and immobilization of the isolated enzyme", African Journal of Mycology and Biotechnology, 11(3), pp. 51-64 (2003) (English Abstract Only).

Kim, et al., "Swelling behavior of semi-interpenetrating polymer network hydrogels based on chitosan and polyacrylamide", Journal of Macromolecular Science, Part A: Pure and Applied Chemistry, A42(8), pp. 1073-1083 (2005).

Kim, et al., Synthesis and characteristics of semi-interpenetrating polymer network hydrogels based on chitosan and poly(hydroxyethyl methacrylate), Journal of Applied Polymer Science, 96(1), pp. 86-92 (2005).

Kubo, et al., "Control of phytic acid-zinc complexing by addition of chitosan", Nippon Nogei Kagaku Kaishi, 76(7), pp. 622-628 (2002) (English Abstract Only).

Lu, et al., "Preparation and characterization of nanocrystalline hydroxyapatite/chitosan-chondroitin sulfate composites", Fuhe Cailiao Xuebao Bianjibu, 24(1), pp. 110-115 (2007) (English Abstract Only).

Martins, et al., "Application of chitosan functionalized with 8-hydroxyquinoline: determination of lead by flow injection flame atomic absorption spectrometry", Microchimica Acta, 150(1), pp. 27-33 (2005).

Miyaoka, et al., Fermentation production of chitosan by using molds in Mucoraceae and some properties of the isolated chitosan, Kichin, Kitosan Kenkyu, 10(1), pp. 13-20 (2004) (English Abstract Only).

Ng, et al., "Formation of chitosan hydroxyapatite composites in the presence of different organic acids", Advances in Chitin Science, 7, pp. 39-42 (2003) (English Abstract Only).

Norris, et al., "Sorption of fluoracetate (compound 1080) by colestipol, activated charcoal and anion-exchange resins In vitro and gastrointestinal decontamination in rats", Veterinary and Human Toxicology, 42(5), pp. 269-275 (2000).

Pang, et al., "Screening of chitosanase-producing strain and research on its fermentation conditions", Zhongguo Haiyang Daxue Xuebao, Ziran Kexueban, 35(2), pp. 287-292 (2005) (English Abstract Only).

Qiu, et al., "Screening, identification of chitosanase-producing microorganism and optimization of its fermentation conditions", Zhejiang Gongye Daxue Xuebao, 33(2), pp. 148-151 (2005) (English Abstract Only).

Qu, et al., "Encapsulation of isotope on novel β-emitting poly(ethylene terephthalate) surfaces", Journal of Biomedical Materials Research, 57(4), pp. 619-623 (2001).

Qu, et al., "Novel β-emitting poly (ethylene terephthalate) surface modification", Journal of Biomedical Materials Research, 52(3), pp. 492-497 (2000).

Wang, et al., "Bone repair in radii and tibias of rabbits with phosphorylated chitosan reinforced calcium phosphate cements", Biomaterials, 23(21), pp. 4167-4176 (2002) (English Abstract Only).

Wang, et al., "Screening, identification, and incubation condition of chitosanase-producing Pseudomonas", Gongye Weishengwu, 30(4), pp. 32-36 (2000) (English Abstract Only).

Wang, et al., "Structural characterization of phosphorylated chitosan and their applications as effective additives of calcium phosphate cements", Biomaterial, 22(16), pp. 2247-2255 (2001).

Wang, et al., "The effects of S-chitosan on the physical properties of calcium phosphate cements", Journal of Bioactive and Compatible Polymers, 18(1), pp. 45-57 (2003) (English Abstract Only).

Xia, et al., "Simultaneous determination of three components in chitosan hemostatic sponge by RP-HPLC", Zhongguo Yaoshi (Wuhan, China), 9(4), pp. 314-316 (2006) (English Abstract Only).

Tharanathan et al, Chitin—The Undisputed Biomoledcule of Great Potential, *Crit. Reviews in Food Sci. & Nutrition*, 43(1):61-87, (2003).

Lowry and Lopez, The Determination of Inorganic Phosphate in the Presence of Labile Phosphate Esters, *J. Biol. Chem.*, 162:421-428, (1946).

International Search Report for PCT/US08/059634, Jan. 15, 2009.

* cited by examiner

PHOSPHATE-BINDING CHITOSAN AND USES THEREOF

BACKGROUND OF THE INVENTION

Like other diseases for which there is no cure, chronic kidney disease takes an ever-increasing toll on patients who have it. As the disease progresses, the kidney becomes less efficient at removing various ions from the blood. Among these ions is phosphate, which can form insoluble particles when combined with calcium. In end-stage renal disease, the final stage of chronic kidney disease, kidney function is so compromised that phosphate levels in the blood (serum) become markedly elevated. This condition, known as hyperphosphatemia, carries with it many grave health risks. For example, when serum phosphate and calcium levels are above a certain threshold, hardened deposits may form throughout the body, endangering circulation. It is therefore very important to control serum phosphate levels in patients with end-stage renal disease.

Patients with end-stage renal disease may be advised to eat a diet low in phosphate. However, phosphate is present at some level in almost all the foods we eat. For this reason, phosphate binders were developed. Phosphate binders are compounds taken orally and which act in the gastrointestinal tract to bind phosphate and keep it from being absorbed. Phosphate binders are generally taken with each meal. Phosphate binders known in the art include, for example, various salts of aluminum and calcium, as well as some chemically synthesized crosslinked polymers. There are clinical circumstances in which the administration of aluminum or calcium salts is ill-advised. In animal models, certain crosslinked polymers carry with them elevated risks of carcinogenesis.

SUMMARY OF THE INVENTION

The present invention provides a safe and effective phosphate binder derived from a natural polymer. In particular, the present invention provides, inter alia, phosphate-binding chitosan, compositions containing phosphate-binding chitosan, and methods for treating hyperphosphatemia using chitosan.

In one aspect, the present invention provides a method for removing phosphate from a subject (e.g., a mammalian subject). The method includes administering to the subject a therapeutically effective amount of chitosan. In some embodiments, the therapeutically effective amount of chitosan is administered orally.

In some embodiments, the subject is in need of treatment for hyperphosphatemia. In some embodiments, the subject is in need of treatment for chronic kidney disease and/or end-stage renal disease. In some embodiments, the subject is in need of treatment for one or more disorders of phosphate metabolism and/or impaired phosphate transport function.

In some embodiments, the therapeutically effective amount ranges from about 0.1 to about 10 grams of chitosan per dose. In some embodiments, the therapeutically effective amount ranges from about 0.5 to about 50 grams of chitosan per day.

In some embodiments, chitosan suitable for the invention binds at least about 30 mg phosphate per gram. In some embodiments, the chitosan binds at least about 60 mg phosphate per gram. In some embodiments, the chitosan binds at least about 90 mg phosphate per gram. In some embodiments, the chitosan binds at least about 120 mg phosphate per gram. In some embodiments, the chitosan binds at least about 150 mg phosphate per gram. In some embodiments, the chitosan binds at least about 180 mg phosphate per gram.

In some embodiments, chitosan suitable for the invention is administered in a form of a plurality of particles. In some embodiments, the plurality of particles have a mean volume particle size less than about 100 cubic microns. In some embodiments, the plurality of particles have a median volume particle size less than about 100 cubic microns.

In some embodiments, the plurality of particles include one or more particles having a roundness greater than about 10. In some embodiments, at least about 0.3% of the plurality of particles have a roundness greater than 10. As used herein, "roundness" refers to a measurement describing the shape of a particle. As used in this application, roundness is defined by the following equation:

$$\text{Roundness} = (\text{Perimeter}^2)/(4 * \text{pi} * \text{area})$$

Roundness is typically measured using a digital image of a population of spheres and Image Pro Plus. Circular objects have a roundness=1.

In another aspect, the present invention provides a method for treating hyperphosphatemia. The method includes administering to a subject in need of treatment for hyperphosphatemia a composition comprising chitosan. In some embodiments, the subject is in need of treatment for chronic kidney disease and/or end-stage renal disease. In some embodiments, the subject is in need of treatment for one or more disorders of phosphate metabolism and/or impaired phosphate transport function.

In some embodiments, the composition of the invention includes a therapeutically effective amount of chitosan. In some embodiments, the therapeutically effective amount is from about 0.1 to about 10 grams chitosan per dose. In some embodiments, the therapeutically effective amount is from about 0.5 to about 50 grams chitosan per day.

In some embodiments, chitosan suitable for the invention binds at least about 30 mg phosphate per gram. In some embodiments, the chitosan binds at least about 60 mg phosphate per gram. In some embodiments, the chitosan binds at least about 90 mg phosphate per gram. In some embodiments, the chitosan binds at least about 120 mg phosphate per gram. In some embodiments, the chitosan binds at least about 150 mg phosphate per gram. In some embodiments, the chitosan binds at least about 180 mg phosphate per gram.

In some embodiments, chitosan suitable for the invention is present in a form of a plurality of particles. In some embodiments, the plurality of particles have a mean volume particle size less than about 100 cubic microns. In some embodiments, the plurality of particles have a median volume particle size less than about 100 cubic microns. In some embodiments, the plurality of particles include one or more particles having a roundness greater than about 10. In some embodiments, at least about 0.3% of the plurality of particles have a roundness greater than 10.

In some embodiments, the composition suitable for the invention is administered orally. In some embodiments, the composition is a nutritional supplement. In some embodiments, the composition is administered three times daily with meals.

In some embodiments, the composition further includes a carrier. In some embodiments, the carrier suitable for the invention is selected from the group consisting of a starch, a gum, an alginate, a silicate, dextrose, gelatin, lactose, mannitol, sorbitol, sucrose, tragacanth, cellulose, methyl cellulose, microcrystalline cellulose, a methylhydroxybenzoate, a propylhydroxybenzoate, polyvinylpyrrolidone and talc. In some embodiments, the composition is in a form of a cachet, a hard gelatin capsule, a soft gelatin capsule, an elixir, a lozenge, a pill, a powder, a sachet, a sterile packaged powder, a suspension, a syrup, or a tablet.

In yet another aspect, the present invention provides a composition suitable for treating hyperphosphatemia containing a therapeutically effective amount of chitosan. In some embodiments, the hyperphosphatemia is associated with chronic kidney disease and/or end-stage renal disease. In some embodiments, the hyperphosphatemia is associated with one or more disorders of phosphate metabolism and/or impaired phosphate transport function.

In some embodiments, the therapeutically effective amount is from about 0.1 to about 10 grams chitosan per dose. In some embodiments, the therapeutically effective amount is from about 0.5 to about 50 grams chitosan per day.

In some embodiments, chitosan suitable for the invention binds at least about 30 mg phosphate per gram. In some embodiments, the chitosan binds at least about 60 mg phosphate per gram. In some embodiments, the chitosan binds at least about 90 mg phosphate per gram. In some embodiments, the chitosan binds at least about 120 mg phosphate per gram. In some embodiments, the chitosan binds at least about 150 mg phosphate per gram. In some embodiments, the chitosan binds at least about 180 mg phosphate per gram.

In some embodiments, chitosan suitable for the invention is present in a form of a plurality of particles. In some embodiments, the plurality of particles have a mean volume particle size less than about 100 cubic microns. In some embodiments, the plurality of particles have a median volume particle size less than about 100 cubic microns.

In some embodiments, the plurality of particles include one or more particles having a roundness greater than about 10. In some embodiments, at least about 0.3% of the plurality of particles have a roundness greater than 10.

In some embodiments, the composition is suitable for oral administration. In some embodiments, the composition is a nutritional supplement.

In some embodiments, the composition further includes a carrier. In some embodiments, the carrier is selected from the group consisting of a starch, a gum, an alginate, a silicate, dextrose, gelatin, lactose, mannitol, sorbitol, sucrose, tragacanth, cellulose, methyl cellulose, microcrystalline cellulose, a methylhydroxybenzoate, a propylhydroxybenzoate, polyvinylpyrrolidone and talc. In some embodiments, the composition is in a form of a cachet, a hard gelatin capsule, a soft gelatin capsule, an elixir, a lozenge, a pill, a powder, a sachet, a sterile packaged powder, a suspension, a syrup, or a tablet.

In still another aspect, the present invention provides a nutritional supplement containing chitosan, wherein the chitosan is present in a form of a plurality of particles having a mean volume particle size less than about 100 cubic microns.

In some embodiments, the plurality of particles include one or more particles having a roundness greater than about 10. In some embodiments, at least 0.3% of the plurality of particles have a roundness greater than about 10.

In a further aspect, the present invention provides a nutritional supplement containing chitosan, wherein the chitosan is present in a form of a plurality of particles having a median volume particle size less than about 100 cubic microns. In some embodiments, the plurality of particles have a mean volume particle size less than about 100 cubic microns.

In some embodiments, the plurality of particles include one or more particles having a roundness greater than about 10. In some embodiments, at least 0.3% of the plurality of particles have a roundness greater than about 10.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

DETAILED DESCRIPTION OF THE INVENTION

The present invention provides compositions and methods for removing phosphate from a subject using chitosan. The present invention also provides compositions and methods for treating hyperphosphatemia using a therapeutically effective amount of chitosan.

Various aspects of the invention are described in detail in the following sections. The use of sections is not meant to limit the invention. Each section can apply to any aspect of the invention. In this application, the use of "or" means "and/or" unless stated otherwise.

Phosphate-Binding Chitosan

Chitosan suitable for the invention is a linear polysaccharide composed of β-(1-4)-linked D-glucosamine (deacetylated unit) and N-acetyl-D-glucosamine (acetylated unit). Chitosan typically has a molecular weight of approximately $10^4$ to $10^6$ dalton or higher. Chitosan is also referred to as poly-D-glucosamine; poly-[1-4]-β-D-glucosamine or deacetylated chitin.

Typically, chitosan is derived from chitin $(C_8H_{13}O_5N)_n$, a long-chain polymer of a N-acetylglucosamine (a derivative of glucose) isolated from natural sources (e.g., cell walls of fungi, the exoskeletons of arthropods) by complete or partial deacetylation and partial depolymerization. The deacetylation of chitin to chitosan can be performed in hot concentrated NaOH solution (40-50%). Chitosan is also commercially available, for example, from Pronova Biopolymer, Inc. (Portsmouth, N.H.), e.g., as SEACURE 142, 242 or 342; from Vanson, Inc. (Redmond, Wash.) under the tradenames "Chitosan;" and from Primex Ingredients SA (Avaldsnes, Norway) under the tradenames "Chitoclear." Other chitosan suppliers include, but are not limited to, Acroyali Holdings Qingdao Co., Ltd. (Qingdao, China); AIDP, Inc. (City of Industry, Calif.); AK Biotech, Ltd. (Jinan, China); AK Scientific, Inc. (Mountain View, Calif.); Barrington Chemical Corporation (Harrison, N.Y.); Beckmann Chemikalien KG (Bassum, Germany); Carbomer, Inc. (San Diego, Calif.); CCS CHEM. Co., Ltd. (Zhejiang, China); Dayang Chemicals Co., Ltd. (Hangzhou, China); DNP International (Whittier, Calif.); Donboo Amino Acid Co., Ltd. (Jiangsu, China); Eco-Tag Comercial Ltd. (Cruz Alta, Brazil); Federal Laboratories Corporation (Alden, N.Y.); Fortune Bridge Co., Inc. (Elmont, N.Y.); Gallard-Schlesinger Industries, Inc. (Plainview, N.Y.); Hongkong Henry Industry Co., Ltd. (ZheJiang, China); Jiagen Biotechnologies, Inc. (Quebec, Canada); Jinan Haohua Industry Co., Ltd. (Shandong, China); Kinbester Co., Ltd. (Xiamen, China); Kingreat Chemistry Co., Ltd. (Xiamen, China); Marcor Development Corporation (Carlstadt, N.J.); Marine Chemicals (Kerala, India); Nantong Chem-Tech. (Group) Co., Ltd. (Nantong, China); Ningbo Innopharmchem Co., Ltd. (Ningbo, China); Ningbo Pangs Lanza International Co., Ltd. (Zhejiang, China); Nutriland Group Inc. (Torrance, Calif.); NutriScience Innovations, LLC (Trumbull, Conn.); Orcas International, Inc. (Flanders, N.J.); Pacific Rainbow International, Inc. (City of Industry, Calif.); Panvo Organics Pvt. Ltd. (Tamil Nadu, India); Parchem Nutrition, Inc. (White Plains, N.Y.); Sears Phytochem Ltd. (Madhya Pradesh, India); SeaTech Bioproducts (Shrewsbury, Mass.); Shanghai Freemen Chemicals Co., Ltd (Shanghai, China); Shanghai Mintchem Development Co., Ltd. (Shanghai, China); Shanghai Nicechem Co., Ltd. (Shanghai, China); Shanghai Sunwise Chemical Co., Ltd. (Shanghai, China); Shanghai Wellhoned Biotech Co., Ltd. (Shanghai, China); Sinosale Hebei Co., Ltd. (Shijiazhuang, China); Spectrum Chemicals & Laboratory Products (Gardena, Calif.); Stryka Botanics (Hillsborough, N.J.); Vitajoy Bio-tech Co., Ltd. (Suzhou, China); Wilke Resources, Inc. (Lenexa, Kans.); Wintersun Chemical (Ontario, Calif.); Wright Group (Crowley, La.); Xiamen Topusing Chemical Co., Ltd. (Xiamen, China).

Chitin, chitosan and chitin derivatives are further described in Tharanathan et al., *Crit. Reviews in Food Sci. & Nutrition*, 43(1), pp. 61-87 (2003), which is incorporated herein by reference.

Chitosan and chitin derivatives are often described according to the degree of de-acetylation within the polysaccharide. Chitosan suitable for the invention may have a range of degrees of de-acetylation. In some embodiments, chitosan suitable for the invention has a higher degree of de-acetylation. In some embodiments, the degree of de-acetylation may be at least about 50% (e.g., at least about 60%, or at least about 70%, or at least about 80%, or at least about 85%, or at least about 87.5%, or at least about 90%, or at least about 92.5%, or at least about 95%, or at least about 97.5%, or at least about 98%, or at least about 99%, or at least about 99.5%, or at least about 99.9%). In some embodiments, the degree of de-acetylation may range between 50% and 99.9% (e.g., between 50% and 99%, or between 75% and 99.9%, or between 85% and 99.9%, or between 87.5% and 99.9%, or between 87.5% and 97.5%, or between 87.5% and 95%, or between 90% and 99.9%, or between 90% and 95%, or between 95% and 99.9%, or between 95.5% and 97.5%, or between 97% and 99.9%, or between 98% and 99.9%, or between 98% and 99.5%, or between 99.5% and 99.9%).

Chitosan suitable for the present invention also includes chitosan derivatives. Exemplary chitosan derivatives include, but are not limited to, medium or long chain N-alkyl- or N-alkanoyl-chitosan, or water-soluble chitosan. The term "medium chain N-alkyl- or N-alkanolyl" refers to $C_{8-13}$-N-alkyl- or -N-alkanolyl chains, the term "long chain N-alkyl- or N-alkanoyl" refers to $C_{14-18}$-N-alkyl- or -N-alkanolyl chains. Examples of water-soluble chitosan include, but are not limited to, CM-chitosan (carboxymethyl-chitosan), S-chitosan (oligosaccharide-chitosan), SCM-chitosan (N-sulfide derivative of N-deacetylated CM chitin), HP-chitosan (hydroxyl-propyl-chitosan).

Suitable chitosan for the invention also includes any conventional salts of chitosan. Examples of salts of chitosan include those with organic acids such as lower alkanoic acids, as well as mineral acids such as HCl and $H_2SO_4$.

Suitable chitosan for the invention also includes any conventional pharmaceutically acceptable acid of chitosan such as acetic, citric, formic and tartaric acid.

Suitable chitosan for the invention further includes modified chitosan. As used herein, "modified chitosan" refers to the chitosan obtained from the subsequent treatment of the initial product obtained from chitin. Exemplary modified chitosan includes, but is not limited to, semi-crystalline, micro-crystalline, and nanoparticulate chitosan. Processes for obtaining modified chitosan are known in the art. Exemplary processes are described in U.S. Pat. Nos. 5,770,187, 6,740,752, 6,638,918, 7,288,532, and PCT publications WO 01/32751, WO 00/47177, the teachings of all of which are hereby incorporated by reference.

In some embodiments, chitosan suitable for the invention binds at least about 30 mg phosphate per gram chitosan. In some embodiments, chitosan suitable for the invention binds at least about 60 mg phosphate per gram. In some embodiments, chitosan suitable for the invention binds at least about 90 mg phosphate per gram. In some embodiments, chitosan suitable for the invention binds at least about 120 mg phosphate per gram. In some embodiments, chitosan suitable for the invention binds at least about 150 mg phosphate per gram. In some embodiments, chitosan suitable for the invention binds at least about 180 mg phosphate per gram chitosan. In some embodiments, chitosan suitable for the invention binds at least about 210 mg phosphate per gram. In some embodiments, chitosan suitable for the invention binds at least about 240 mg phosphate per gram.

Without wishing to be bound by any theories, it is contemplated that chitosan bind and remove phosphate through an ion exchange process. As used herein, the term "ion exchange" has its ordinary meaning in the chemical and/or pharmaceutical field. In particular, ion exchange can be a process including the release of one or more anions ionically bound to a cationic polymer and the subsequent ionic binding of another one or more anions to the polymer. As a non-limiting example, ion exchange includes the release of one or more chloride ions from a polymer such as chitosan and the subsequent binding of one or more phosphate, hydrogen phosphate, and/or dihydrogen phosphate ions to the polymer.

Particles of Chitosan

In particular, chitosan suitable for the present invention may be in a form of particles. In some embodiments, chitosan suitable for the invention are present in a form of a plurality of particles. The chitosan particulates suitable for the invention can have a broad particle size distribution. Typically, the chitosan particles can be characterized by a mean volume particle size, and/or a median volume particle size. In some embodiments, the chitosan particles suitable for the invention can have a mean volume particle size less than about 300 cubic microns, or less than about 250 cubic microns, or less than 200 cubic microns, or less than 150 cubic microns, or less than about 100 cubic microns, or less than about 75 cubic microns, or less than about 50 cubic microns. As used herein, 1 cubic micron equals to 1 $\mu m^3$. In some embodiments, the chitosan particles have a mean volume particle size less than about 100 cubic microns.

In other embodiments, the chitosan particles suitable for the invention can have a median volume particle size less than about 300 cubic microns, or less than about 250 cubic microns, or less than 200 cubic microns, or less than 150 cubic microns, or less than about 100 cubic microns, or less than about 75 cubic microns, or less than about 50 cubic microns. As used herein, 1 cubic micron equals to 1 $\mu m^3$. In some embodiments, the chitosan particles have a median volume particle size less than about 100 cubic microns.

In some embodiments, the chitosan particles suitable for the invention may have combinations of median volume particle size and mean volume particle size as described above. For example, the chitosan particles suitable for the invention may have a median volume particle size less than about 100 cubic microns and a mean volume particle size less than about 100 cubic microns.

A chitosan particle can also be characterized by a roundness. As used herein, the term "roundness" has its ordinary meaning in the particle size and shape measurement arts. As used in this application, roundness is defined by the following equation:

$$\text{Roundness} = (\text{Perimeter}^2)/(4 * \text{pi} * \text{area})$$

Roundness is typically measured using a digital image of a population of spheres and Image Pro Plus. Circular objects have a roundness=1.

Typically, chitosan particles suitable for the invention can have a range of roundness. For example, a plurality of chitosan particles suitable for the invention may have particles with a roundness greater than 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, or greater. In some embodiments, a plurality of chitosan particles suitable for the invention include one or more particles having a roundness greater than 10. In some embodiments, at least about 0.1% of the plurality of chitosan particles used in a composition of the invention have a roundness greater than 10. In some embodiment, at least about 0.2% of the plurality of chitosan particles used in a composition of the invention have a roundness greater than 10. In some embodiment, at least about 0.3% of the plurality of chitosan particles used in a composition of the invention have a roundness greater than 10. In some embodiment, at least about 0.4% of the plurality of chitosan particles used in a composition of the invention have a roundness greater than 10. In some embodiment, at least about 0.5% of the plurality of chitosan particles used in a composition of the invention have a roundness greater than 10. In some embodiment, at least about 1.0% of the plurality of chitosan particles used in a composition of the invention have a roundness greater than 10. In some embodiment, at least about 5.0% of the plurality of chitosan particles used in a composition of the invention have a roundness greater than 10.

In some embodiments, the chitosan particulates suitable for the invention are cationic particulates. In some embodiments, the chitosan particulates suitable for the invention can be anionic/cationic amphoteric particulates or anionic particulates. Processes for producing chitosan particulates are well known in the art. For example, materials in which chitosan having a primary amino group as a base can be dissolved in an acid and the resultant solution can be dropped into an alkaline coagulation fluid to produce cationic particulates. As another non-limiting example, chitosan solutions or dispersions can be mechanically treated to generate particulates.

Treatment of Hyperphosphatemia

Phosphate-binding chitosan as described above can be used to treat hyperphosphatemia. As used herein, the term "hyperphosphatemia" refers to a higher than normal blood level of phosphorous. In human adults, the normal range for blood phosphorous is approximately 2.5-4.5 mg/dL (i.e., 2.5-4.5 mg/100 ml). Typically, an individual with hyperphosphatemia condition has fasting serum phosphorus concentration higher than 5.0 mg/dL (e.g., higher than 5.5 mg/dL, 6.0 mg/dL, 6.5 mg/dL, or 7.0 mg/dL). Methods for measuring phosphate concentrations are well known in the art. For example, phosphate concentrations can be quantitated by the method of Lowry and Lopez, *J. Biol. Chem.* 162: 421-428. The hyperphosphatemia condition, especially if present over extended periods of time, leads to severe abnormalities in calcium and phosphorus metabolism and can be manifested by aberrant calcification in joints, lungs, and eyes.

Hyperphosphatemia is associated with various diseases or medical conditions including, but not limited to, diseases associated with inadequate renal function such as, for example, chronic kidney disease and/or end-stage renal disease, hypoparathyroidism, and other disorders of phosphate metabolism and/or impaired phosphate transport function.

As used herein, an "individual," "patient" or "subject" being treated includes a human or a non-human such as, a non-human mammalian subject including, but not limited to, a bovine, cat, dog, ferret, gerbil, goat, guinea pig, hamster, horse, mouse, nonhuman primate, pig, rabbit, rat, or sheep.

The term, "treat" or "treatment," as used herein, includes achieving a therapeutic benefit and/or a prophylactic benefit. By therapeutic benefit is meant eradication, amelioration, or prevention of the underlying disorder being treated. For example, in a hyperphosphatemia patient, therapeutic benefit includes eradication or amelioration of the underlying hyperphosphatemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. In particular, treating hyperphosphatemia includes reducing or decreasing serum phosphate concentration. As used herein, the terms "reduce" or "decrease," and grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same condition of hyperphosphatemia as the individual being treated. For prophylactic benefit, the composition of the invention may be administered to a patient at risk of developing hyperphosphatemia or to a patient reporting one or more of the physiological symptoms of hyperphosphatemia, even though a diagnosis of hyperphosphatemia may not have been made.

In general, a method of treating hyperphosphatemia includes administering to a subject a therapeutically effective amount of chitosan. As used herein, the term "therapeutically effective amount" refers to an amount effective to achieve therapeutic or prophylactic benefit as described above. The therapeutically effective amount can be administered in a single dose or in a series of doses separated by appropriate time intervals, such as hours or days. For example, a therapeutically effective amount is commonly administered in a dosing regimen that may comprise multiple unit doses. An appropriate unit dose within an effective dosing regimen is also referred to as "therapeutically effective dose."

The actual amount effective for a particular application will depend on the condition being treated (e.g., the disease or disorder and its severity, and the age and weight of the patient to be treated) and the route of administration. Determination of an effective amount is well within the capabilities of those skilled in the art, especially in light of the disclosure herein. For example, the effective amount for use in humans can be determined from animal models. For example, a dose for humans can be formulated to achieve circulating and/or gastrointestinal concentrations that have been found to be effective in animals. In some embodiments, a therapeutically effective amount of chitosan can be at least about 0.1 grams per dose, or at least 2 grams per dose, at least 4 grams per dose, or at least 6 grams per dose, or at least, 8 grams per dose, or at least 10 grams per does, or at least 15 grams per dose, or at least 20 grams per dose. In some embodiments, a therapeutically effective amount of chitosan is from about 0.1 to about 10 grams per dose. In some embodiments, a therapeutically effective amount of chitosan is from about 0.1 to about 20 grams per dose. In some embodiments, a therapeutically effective amount of chitosan is from about 0.1 to about 5 grams per dose. In some embodiments, the therapeutically effective amount of chitosan can be at least about 0.5 grams per day, or at least 5 grams per day, at least 10 grams per day, or at least 15 grams per day, or at least 20 grams per day, or at least 25 grams per day, or at least 30 grams per day, or at least 35 grams per day, or at least 40 grams per day, or at least 45 grams per day, or at least 50 grams per day, or at least 55 grams per day, or at least 60 grams per day. In some embodiments, the therapeutically effective amount of chitosan ranges from about 0.5 to about 50 grams per day. In some embodiments, the therapeutically effective amount of chitosan is from about 0.5 to about 25 grams per day. In some embodiments, the therapeutically effective amount of chitosan is from about 0.5 to about 100 grams per day. In some embodiments, the therapeutically effective amount of chitosan is from about 10 to about 150 grams per day.

In some embodiments, the chitosan of the invention is used together with one or more other phosphate binders to treat hyperphosphatemia. For example, the chitosan may be used together with aluminium hydroxide (Alucaps®), calcium carbonate (Calcichew®, Titralac®), calcium acetate (Phosex®, PhosLo®), lanthanum carbonate (Fosrenol®), or sevelamer (Renagel®, Renvela®).

Compositions Containing Phosphate-Binding Chitosan

The chitosan used for therapeutic and/or prophylactic benefits can be administered alone or in the form of a composition as described herein. A composition of the invention typically contains a therapeutically effective amount (or a therapeutically effective dose) of phosphate-binding chitosan as described above. Typically, the percentage of chitosan in a composition of the invention is at least about 0.005% by weight of the composition (e.g., at least about 0.1%, 0.5%, 1.0%, 1.5%, 2%, 2.5%, 3%, 3.5%, 4%, 4.5%, 5%, 10%, 15%, 20%, 25%, 30% or higher). In some embodiments, the percentage of chitosan in a composition of the invention ranges from about 0.1% to about 30% based on the weight of the composition. In some embodiments, the percentage of chitosan in a composition of the invention ranges from about 0.1% to about 10% based on the weight of the composition. In some embodiments, the percentage of chitosan in a composition of the invention ranges from about 0.2% to about 5% based on the weight of the composition. In some embodiments, the percentage of chitosan in a composition of the invention ranges from about 0.35% to about 1.0% based on the weight of the composition.

Typically, a composition of the invention further includes a carrier. A carrier suitable for the invention is also referred to as a pharmaceutically acceptable carrier or a carrier-diluent. A carrier may be a solid, semi-solid or liquid material which acts as an excipient, medium, and/or vehicle for chitosan. For example, a composition of the invention can be in a solid or liquid medium. For example, chitosan may be enclosed within a carrier, such as a capsule, paper, sachet or other container. In particular, a suitable carrier, excipient, or diluent may be a starch, a gum, an alginate, a silicate, dextrose, gelatin, lactose, mannitol, sorbitol, sucrose, tragacanth, cellulose, methyl cellulose, microcrystalline cellulose, a methylhydroxybenzoate, a propylhydroxybenzoate, polyvinylpyrrolidone or talc.

The chitosan can be administered by injection, topically, orally, transdermally, or rectally. The composition containing chitosan can be formulated to suit the mode of administration. In some embodiments, a composition of the present invention is formulated for oral administration. For example, a composition according to the invention may be in a form of a cachet, a hard gelatin capsule, a soft gelatin capsule, an elixir, a lozenge, a pill, a powder, a sachet, a sterile packaged powder, a suspension, a syrup, a tablet, a capsule, solution, or emulsion, to name but a few.

In some embodiments, a composition of the invention can be a food, a drink, or a nutritional, food or dietary supplement. In one embodiment, the composition is a nutritional supplement. As used herein, "a nutritional supplement" is a preparation formulated to supply nutrients (including, but not limited to, vitamins, minerals, fatty acids or amino acids) that are missing or not consumed in sufficient quantity in a person's or animal's diet. As used in this application, a nutritional supplement is also referred to as "a food supplement" or "a dietary supplement."

In some embodiments, the composition of the invention is a nutritional supplement for a person's diet. The nutritional supplement can be administered with or without meals and can be administered once daily, twice daily, three times daily, once every other day, twice a week, once a week, or at a variable intervals. In some embodiments, the nutritional supplements can be administered three times daily with meals. Supplements may be in various forms including, for example, powders, liquids, syrups, pills, encapsulated compositions, etc.

In some embodiments, the composition of the invention is a nutritional supplement for an animal's diet, such as, a feed or pet food used with another feed or pet food to improve the nutritive balance or performance of the total. Contemplated supplements include compositions that are fed undiluted as a supplement to other feeds or pet foods, offered ad libitum with other parts of an animal's ration that are separately available, or diluted and mixed with an animal's regular feed or pet food to produce a complete feed or pet food.

In another embodiment, a composition of the invention can be a treat for animals. Treats include, for example, compositions that are given to an animal to entice the animal to eat during a non-meal time. Contemplated treats for canines include, for example, dog bones. Treats may be nutritional, wherein the composition comprises one or more nutrients, and may, for example, have a composition as described above for food. Non-nutritional treats encompass any other treats that are non-toxic. Chitosan can be coated onto the treat, incorporated into the treat, or both.

Typically, the chitosan and other ingredients of the composition are present at concentrations that do not impart, when combined, an odor or flavor that causes the intended animal to perceive the composition to be unacceptable for consumption. In many instances, a desirable odor and flavor can be achieved using aroma or flavor enhancers.

The present invention, thus generally described, will be understood more readily by reference to the following examples, which are provided by way of illustration and are not intended to be limiting of the present invention.

EXAMPLES

Example 1

Phosphate-Binding Assay

Phosphate concentrations were quantitated by the method of Lowry and Lopez, *J. Biol. Chem.*, 162: 421-428. To determine phosphate binding to chitosan powder, 20 mg chitosan was weighed into a 12×75 mm glass tube. 3.0 ml of distilled water and 50 µl of 0.53M monobasic potassium phosphate were added. The tube was sealed with plastic wrap and placed on a Lab-Tek Aliquot mixer to mix for 1 hour at room temperature. The chitosan was then allowed to settle by gravity.

3.0 ml of acetate buffer (0.1N acetic acid, 0.025N sodium acetate) was added into a new clean, dry, and optically matched 12×75 mm glass tube. 50 μl of supernatant was taken from the chitosan tube as prepared above and mixed into the acetate buffer. Next, 0.30 ml of 1% ascorbic acid was added with mixing followed by 0.30 ml of 1% ammonium molybdate in 0.05N sulfuric acid with mixing. The absorbance at 700 nm was measured in a Spectronic 20 spectrophotometer 10 minutes after adding the molybdate to determine the amount of phosphate remaining in the chitosan supernatant. A blank tube containing no chitosan and no phosphate and a phosphate standard containing no chitosan were run through the entire assay simultaneously as controls.

To calculate the amount of phosphate bound to chitosan, the absorbance of the blank was subtracted from the absorbance of all the other samples to obtain the corrected absorbance. The phosphate concentration remaining in the chitosan supernatant was calculated on the basis of the corrected absorbance of the phosphate standard compared to that of the chitosan sample. The total amount of phosphate remaining in the chitosan supernatant was then subtracted from the total amount of the initial phosphate to obtain the amount bound to chitosan and expressed as mg phosphate bound per gram of chitosan powder.

Exemplary phosphate-binding results are summarized in Table 1.

TABLE 1

Exemplary phosphate-binding activities

| Sample | PO$_4$ binding, mg/g |
|---|---|
| A | $0 < y \leq 30$ |
| B | $0 < y \leq 30$ |
| C | $0 < y \leq 30$ |
| D | $0 < y \leq 30$ |
| E | $0 < y \leq 30$ |
| F | $30 < y \leq 60$ |
| G | $30 < y \leq 60$ |
| H | $60 < y \leq 90$ |
| I | $60 < y \leq 90$ |

The degree of de-acetylation was also determined using standard methods and exemplary results are summarized in Table 2.

TABLE 2

Exemplary results of de-acetylation degree

| Sample | % De-acetylation |
|---|---|
| A | $87.5 < x \leq 91.5$ |
| B | $87.5 < x \leq 91.5$ |
| C | $87.5 < x \leq 91.5$ |
| D | $87.5 < x \leq 91.5$ |
| E | $87.5 < x \leq 91.5$ |
| F | $91.5 < x \leq 94.7$ |
| G | $91.5 < x \leq 94.7$ |
| H | $94.7 < x \leq 97.1$ |
| I | $94.7 < x \leq 97.1$ |

The exemplary degrees of de-acetylation shown in Table 2 are non-limiting examples. Indeed, chitosan samples with a range of degree of de-acetylation can be used to bind phosphate, including chitosan samples with de-acetylation degree lower than 87.5% (e.g., lower than 85%, 80%, 75%, 70%, 65%, 60%, 55%, 50%, or lower).

Without wishing to be bound by any theory, it is however contemplated that higher degree of de-acetylation may enhance phosphate-binding activity of chitosan. Chitosan samples with higher degrees of de-acetylation can be prepared and the predicted phosphate-binding activities are shown in Table 3.

TABLE 3

Additional exemplary phosphate-binding activities

| Sample | % Deacetylation (x) | PO$_4$ binding (y), mg/g |
|---|---|---|
| J | $97.1 < x \leq 98.7$ | $90 < y \leq 120$ |
| K | $98.7 < x \leq 99.5$ | $120 < y \leq 150$ |
| L | $99.5 < x \leq 99.9$ | $150 < y \leq 180$ |
| M | $99.9 < x$ | $180 < y \leq 210$ |

Example 2

The Size and Shape of Chitosan Particles and their Phosphate-Binding Abilities

Certain samples of chitosan were subjected to particle size and shape analysis using techniques known in the particle size measurement art. For example, samples of chitosan particles can be analyzed using a Nikon microscope and Image-Pro Plus.

To analyze a sample using Image-Pro Plus, the sample was first dispersed into a carrier fluid. It was then put under the microscope and the magnification was determined. In the Image-Pro Plus program, refining adjustments were made to get an optimal image with good contrast so that the program can distinguish the particles from the background. Typically, 100 images were then taken at random to get an unbiased result. Typically, at least 300 particles were needed to count in the 100 images.

Once the images were collected, a Macro was run on Image-Pro Plus to count the particles and calculate the specific statistics as needed (e.g., roundness, area or size). For example, roundness was calculated by the program using the formula (perimeter$^2$)/(4*p*area). Circular objects have a roundness=1.

The size distribution of a chitosan sample was typically characterized by a mean volume particle size and/or a median volume particle size.

The phosphate-binding abilities of chitosan samples were determined as described in Example 1.

A possible relationship between particle size and the presence or absence of phosphate-binding activity was determined. Exemplary results are summarized in Table 4.

TABLE 4

| Chitosan sample description | Volume mean, μm$^3$ | Volume median, μm$^3$ |
|---|---|---|
| Phosphate binder | <100 | <100 |
| Phosphate non-binder alpha | >100 | >100 |
| Phosphate non-binder beta | >100 | >100 |

A possible relationship between particle shape (roundness) and the presence or absence of phosphate-binding activity was also determined. Exemplary results are summarized in Table 5.

TABLE 5

| Chitosan sample description | Max. particle roundness | % particles with roundness greater than 10 |
|---|---|---|
| Phosphate binder | >10 | 0.3% |
| Phosphate non-binder alpha | <10 | 0 |
| Phosphate non-binder beta | <10 | 0 |

Example 3

Treatment of Hyperphosphatemia Using Chitosan

The following human patients suffering from hyperphosphatemia are treated with chitosan as described below.

Human patient No. 1 has a serum phosphorus concentration between about 5.5 and about 7.5 mg/dL and has not taken a phosphate binder prior to the treatment. A composition containing about 4 grams of chitosan sample I from Table 1 is orally administered three times daily with meals.

Human patient No. 2 has a serum phosphorus concentration between about 7.5 and about 9.0 mg/dL and has not taken a phosphate binder prior to the treatment. A composition containing about 6 grams of chitosan sample I from Table 1 is orally administered three times daily with meals.

Human patient No. 3 has a serum phosphorus concentration greater than about 9.0 mg/dL and has not taken a phosphate binder prior to the treatment. A composition containing about 8 grams of chitosan sample I from Table 1 is orally administered three times daily with meals.

Human patient No. 4 suffers from hyperphosphatemia and has been taking one 667-mg calcium acetate tablet per meal. A composition containing about 2 grams of chitosan sample K from Table 3 is orally administered three times daily with meals, instead of the one 667-mg calcium acetate tablet per meal.

Human patient No. 5 suffers from hyperphosphatemia and has been taking two 667-mg calcium acetate tablets per meal. A composition containing about 3 grams of chitosan sample K from Table 3 is orally administered three times daily with meals, instead of the two 667-mg calcium acetate tablets per meal.

Human patient No. 6 suffers from hyperphosphatemia and has been taking three 667-mg calcium acetate tablets per meal. A composition containing about 5 grams of chitosan sample K from Table 3 is orally administered three times daily with meals, instead of the three 667-mg calcium acetate tablets per meal.

Human patient No. 7 has a serum phosphorus level between 5.5 and 6.0 mg/dL and has not taken a phosphate binder prior to the treatment. A composition containing about 0.15 grams of chitosan sample M from Table 3 is orally administered three times daily with meals.

In each of the cases, the patient's hyperphosphatemia is controlled. In some cases, the patent's blood phosphate level is lowered after chitosan treatment. The dosing can be adjusted during treatment based on the patient's condition and the blood phosphorus level. Typically, the dosing regimens are maintained unchanged when the human patients' serum phosphorus levels are reduced to and remain in the range from 3.5 to 5.5 mg/dL, in which case the patient's hyperphosphatemia is being controlled.

Equivalents

The foregoing has been a description of certain non-limiting embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description are introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

INCORPORATION OF REFERENCES

All publications and patent documents cited in this application are incorporated by reference in their entirety to the same extent as if the contents of each individual publication or patent document were incorporated herein.

What is claimed is:

1. A method for treating hyperphosphatemia, the method comprising administering to a subject in need of treatment a composition comprising a therapeutically effective amount of chitosan,
wherein the chitosan has a degree of de-acetylation greater than about 95% and is characterized with an ability to binds at least about 60 mg phosphate per gram of chitosan in an in vitro phosphate-binding assay, and
wherein the therapeutically effective amount of chitosan ranges from 0.5 to about 25 grams per day.

2. The method of claim 1, wherein said subject is in need of treatment for chronic kidney disease and/or end-stage renal disease.

3. The method of claim 1, wherein said subject is in need of treatment for one or more disorders of phosphate metabolism and/or impaired phosphate transport function.

4. The method of claim 1, wherein the chitosan is administered from about 0.1 to about 10 grams per dose.

5. The method of claim 1, wherein the therapeutically effective amount is about 5 grams per day.

6. The method of claim 1, wherein the chitosan is characterized with the ability to binds at least about 90 mg phosphate per gram of chitosan in the in vitro phosphate-binding assay.

7. The method of claim 1, wherein the chitosan is characterized with the ability to binds at least about 120 mg phosphate per gram of chitosan in the in vitro phosphate-binding assay.

8. The method of claim 1, wherein the chitosan is characterized with the ability to binds at least about 150 mg phosphate per gram of chitosan in the in vitro phosphate-binding assay.

9. The method of claim 1, wherein the chitosan is characterized with the ability to binds at least about 180 mg phosphate per gram of chitosan in the in vitro phosphate-binding assay.

10. The method of claim 1, wherein the chitosan is present in a form of a plurality of particles.

11. The method of claim 10, wherein the plurality of particles have a mean volume particle size less than about 100 cubic microns.

12. The method of claim 10, wherein the plurality of particles have a median volume particle size less than about 100 cubic microns.

13. The method of claim 10, wherein the plurality of particles comprise one or more particles having a roundness greater than about 10.

14. The method of claim 13, wherein at least about 0.3% of the plurality of particles have a roundness greater than 10.

15. The method of claim 1, wherein the composition is administered orally.

16. The method of claim 1, wherein the composition is a nutritional supplement.

17. The method of claim 16, wherein the composition is administered three times daily with meals.

18. The method of claim 1, wherein the composition further comprises a carrier.

19. The method of claim 18, wherein the carrier is selected from the group consisting of a starch, a gum, an alginate, a silicate, dextrose, gelatin, lactose, mannitol, sorbitol, sucrose, tragacanth, cellulose, methyl cellulose, microcrystalline cellulose, a methylhydroxybenzoate, a propylhydroxybenzoate, polyvinylpyrrolidone and talc.

20. The method of claim 1, wherein the composition is in a form of a cachet, a hard gelatin capsule, a soft gelatin capsule, an elixir, a lozenge, a pill, a powder, a sachet, a sterile packaged powder, a suspension, a syrup, or a tablet.

21. The method of claim 1, wherein the therapeutically effective amount is about 10 grams per day.

22. The method of claim 1, wherein the in vitro phosphate-binding assay uses monobasic potassium phosphate.

* * * * *